United States Patent
Bartlett

(10) Patent No.: US 7,469,572 B2
(45) Date of Patent: Dec. 30, 2008

(54) MEASUREMENT OF MOISTURE VAPOR TRANSFER RATE

(75) Inventor: Alan L. Bartlett, New Braunfels, TX (US)

(73) Assignee: KCI Licensing, Inc., San Antonio, TX (US)

( * ) Notice: Subject to any disclaimer, the term of this patent is extended or adjusted under 35 U.S.C. 154(b) by 0 days.

(21) Appl. No.: 11/775,610

(22) Filed: Jul. 10, 2007

(65) Prior Publication Data

US 2008/0047325 A1   Feb. 28, 2008

Related U.S. Application Data

(60) Provisional application No. 60/831,275, filed on Jul. 17, 2006.

(51) Int. Cl.
*G01N 7/00* (2006.01)
(52) U.S. Cl. .......................... 73/29.01; 73/38
(58) Field of Classification Search ............... 73/73, 73/38, 29.01
See application file for complete search history.

(56) References Cited

U.S. PATENT DOCUMENTS

| | | | | |
|---|---|---|---|---|
| 3,286,509 A | * | 11/1966 | Gluckman et al. | 73/38 |
| 3,572,090 A | * | 3/1971 | Graham et al. | 73/73 |
| 3,886,057 A | * | 5/1975 | Bredeweg | 204/430 |
| 4,581,921 A | * | 4/1986 | Gillespie et al. | 73/73 |
| 6,085,579 A | * | 7/2000 | Herrlein | 73/73 |
| 6,446,495 B1 | * | 9/2002 | Herrlein et al. | 73/73 |
| 6,487,891 B2 | * | 12/2002 | Moretti | 73/38 |
| 7,174,774 B2 | * | 2/2007 | Pawar et al. | 73/73 |

OTHER PUBLICATIONS

Figliola, Richard S., A Proposed Method for Quantifying Low-Air-Loss Mattress Performance By Moisture Transport, Ostomy *Wound Management*, Jan. 2003, pp. 32-42, vol. 49 Issue 1.

Reger, Steven I., Validation Test For Climate Control on Air-Loss Suports, Arch Phys Med Rehabil, May 2001, pp. 597-603, vol. 82.

International Search Report issued in International Application No. PCT/US07/73622, mailed Mar. 28, 2008.

\* cited by examiner

*Primary Examiner*—Daniel S Larkin

(57) ABSTRACT

Systems and methods include a test media, a reservoir containing fluid, and a sensor compared to measure a parameter that is related to an amount of fluid in the test media. Systems and methods may include a comparator to compare the parameter measurement to a parameter set point. Systems and methods may include a control system to control the addition of the fluid to the test media so that the parameter is maintained at a steady state value.

29 Claims, 9 Drawing Sheets rate-of-drying curve, constant drying conditions.

| TIME | ELAPSED TIME (HOURS) | Weight - Water (grams) | Resistance (M ohm) | Normalized Conductivity |
|---|---|---|---|---|
| 8:00 | -0:02 |  | 25 |  |
| 8:02 | 0:00 | 95 | 0.58 | 103.45 |
| 8:07 | 0:05 | 93 | 0.52 | 96.77 |
| 8:14 | 0:12 | 91 | 0.723 | 82.99 |
| 8:27 | 0:25 | 89 | 0.819 | 73.26 |
| 5:30 | 0:28 | 89 | 0.845 | 71.01 |
| 8:40 | 0:38 | 86 | 0.933 | 64.31 |
| 8:45 | 0:43 | 88 | 0.975 | 61.54 |
| 8:50 | 0:48 | 84 | 1.03 | 58.25 |
| 8:55 | 0:53 | 84 | 1.07 | 56.07 |
| 9:00 | 0:58 | 82 | 1.12 | 53.57 |
| 9:06 | 1:04 | 79 | 1.2 | 50.00 |
| 9:12 | 1:10 | 79 | 1.28 | 46.88 |
| 9:19 | 1:17 | 75 | 1.4 | 42.86 |
| 9:28 | 1:26 | 73 | 1.54 | 38.96 |
| 9:37 | 1:35 | 75 | 1.73 | 34.68 |
| 9:45 | 1:43 | 73 | 1.89 | 31.75 |
| 9:50 | 1:48 | 70 | 1.995 | 30.08 |
| 10:25 | 2:23 | 59 | 3.825 | 15.69 |
| 10:39 | 2:37 | 57 | 3.825 | 15.69 |
| 10:50 | 2:48 | 52 | 5.384 | 11.14 |
| 10:55 | 2:53 | 52 | 6.49 | 9.24 |
| 10:55 | 2:54 | 52 | 6.7 | 8.96 |
| 10:57 | 2:55 | 52 | 8.95 | 8.63 |
| 10:58 | 2:56 | 52 | 7.28 | 8.28 |
| 10:59 | 2:57 | 52 | 7.56 | 7.94 |
| 11:00 | 2:58 | 52 | 7.89 | 7.60 |
| 11:01 | 2:59 | 52 | 8.2 | 7.32 |
| 11:02 | 3:00 | 48 | 8.56 | 7.01 |
| 11:03 | 3:01 | 48 | 8.92 | 6.73 |
| 11:04 | 3:02 | 48 | 9.25 | 5.49 |
| 11:05 | 3:03 | 48 | 9.6 | 6.25 |
| 11:06 | 3:04 | 48 | 9.8 | 6.12 |
| 11:07 | 3:05 | 45 | 10.07 | 5.96 |
| 11:08 | 3:06 | 48 | 10.4 | 5.77 |
| 11:09 | 3:07 | 48 | 10.8 | 5.56 |
| 11:10 | 3:08 | 48 | 11.21 | 5.35 |
| 11:11 | 3:09 | 48 | 11.7 | 5.13 |
| 11:12 | 3:10 | 48 | 12.1 | 4.96 |
| 11:13 | 3:11 | 45 | 12.6 | 4.76 |
| 11:14 | 3:12 | 48 | 13.1 | 4.58 |
| 11:15 | 3:13 | 45 | 13.6 | 4.41 |
| 11:15 | 3:14 | 45 | 14.1 | 4.26 |
| 11:17 | 3:15 | 45 | 14.3 | 4.05 |
| 11:18 | 3:16 | 45 | 15.3 | 3.92 |
| 11:19 | 3:17 | 45 | 15.9 | 3.77 |
| 11:20 | 3:18 | 45 | 16.5 | 3.64 |
| 11:23 | 3:21 | 43 | 19.3 | 3.11 |

FIG. 5

MEASUREMENT OF MOISTURE VAPOR TRANSFER RATE

CROSS-REFERENCES TO RELATED APPLICATIONS

This application claims priority to U.S. Provisional Patent Application No. 60/831,275, filed Jul. 17, 2006, which is incorporated by reference herein without disclaimer.

FIELD OF THE INVENTION

The present disclosure relates generally to systems and methods for measuring moisture vapor transfer rates, and more particularly but not by way of limitation to systems and methods for measuring moisture vapor transfer rates for materials used to support patients or other persons.

BACKGROUND

The treatment and/or prevention of pressure ulcers are serious and expensive issues in the health care industry. Pressure ulcer development is related, in part, to the accumulation of heat and perspiration on the skin. Heat and moisture increase skin susceptibility to the damaging effects of pressure and shear and decrease the resiliency of the epidermis to external forces. Ongoing compressive forces on skin tissues are known to promote ischemia with subsequent development of pressure ulcers. Therefore, controlling the microclimate of the skin and providing a quality patient support system appear to be necessary to prevent pressure ulcers.

Currently, low-air-loss (LAL) mattress systems are the most prevalent tools used for pressure ulcer treatment and prevention. LAL mattress systems were developed and are used in the belief that they help to control the microclimate of the skin. These systems have been found to be highly effective in treating and/or preventing pressure ulcers.

Low-air-loss broadly refers to a system comprising a mattress casing, a vapor permeable coverlet with or without lofting or cushioning material, and an air delivery system to move air under the coverlet and, in some cases, to leak through the coverlet. Some LAL mattress systems function as integral parts of patient support systems; whereas, others are not actively coupled.

LAL mattresses typically include a foundation of a series of interconnected air cells that allow air to flow through and exit the mattress. Other common elements include an adjustable pump that can maintain air inflation of the air cells. In addition to the mattress, the LAL mattress system also includes the coverlet (waterproof and/or vapor permeable), and coverlet lofting material (e.g., quilted polyester fabric batting) that attach over the mattress. The coverlet is typically made of a material(s) that is permeable to moisture, is impermeable to bacteria, and is waterproof. Coverlets also function to prevent excessive loss of body heat, have high moisture vapor permeability to minimize/prevent the accumulation of perspiration on the skin, and have high air porosity for removal of excessive body heat through a continuous airflow provided by the LAL mattress. Together, the LAL mattress and the coverlet form the LAL mattress system.

The LAL mattress can further include a fabric cover over the foundation (i.e., the air cells). In some cases, this fabric cover is formed from a Goretex™ fabric. The Goretex™ fabric is liquid impermeable and has significantly higher air-permeable and vapor permeable characteristics as compared to urethane-backed nylon materials used in other mattresses. The Goretex™ fabric moisture vapor transfer characteristics helps to prevent the formation or speed up healing of pressure ulcers in patients by reducing the amount of moisture buildup on the skin and by helping to keep patients cooler by allowing body heat to more easily escape.

LAL mattress systems are intended to remove or reduce the amount of perspiration on the skin of the patient, the evaporation of which provides cooling to control skin microclimate. The two mechanisms that are used by the LAL system to remove moisture and heat are diffusive evaporation and convective evaporation. In diffusive evaporation, moisture is evaporated through and under the coverlet to cool the skin without the need to physically blow air on the patient to keep the skin cool and dry. On the other hand, convective evaporation relies on moving air directly against the skin to evaporate perspiration. Both mechanisms rely on removing moisture away from the patient and the mattress. Some LAL systems incorporate features of both convective and diffusion methods. Either mechanism, however, depends on the LAL mattress system not only drawing moisture away from the patient, but also removing that moisture from the mattress system itself. If this is not accomplished, the patient lies in a damp environment that contributes to skin breakdown and susceptibility to bacterial growth.

Evaporation of moisture off the skin can result in significant cooling of body temperature. In LAL mattress systems low humidity air circulates under the patient's support cover, increasing evaporation and cooling. Although the removal of perspiration on the skin is significant, there are no absolute guidelines on the amount of moisture that should be removed or the decrease in body temperature that should result from the use of an LAL mattress system. Most LAL manufactures agree that the airflow of the system should be at least the amount needed to remove perspiration of an average person at rest in a moderate climate. A typical inactive patient with a body temperature of 37 degrees C. perspires about 600 g/day in a continuous manner. An average prostrate patient provides a mattress pressure loading of approximately 10 mm Hg over the torso area.

Without firm guidelines, physicians must order support systems (e.g., LAL mattress systems) based on cost, claims of the suppliers, and prior experience. Therefore, to improve the selection process of support systems and to further advance the design these systems, measurable parameters that accurately reflect moisture transport from a support systems need to be established and standardized. There are a variety of different designs for LAL mattress and other support systems. But for the variety of designs, there is yet to be an acceptable reproducible standard on which to base their performance and/or assess the anticipated clinical effect of the support systems.

A moisture vapor transfer (MVT) rate, or flux, is one parameter that is currently measured in assessing the performance of LAL mattress and other support systems. The MVT rate can be measured as grams (of human perspiration) per (Meter$^2$) per (hour). Typically, the MVT rate is measured from a support system using a batch process. In this batch process, a fixed amount of a test fluid (e.g., water) is adsorbed in a test media (e.g., a non-woven towel) and pressure and heat are applied to simulate a patient's weight, heat, and perspiration load at the patient-mattress interface of the support system. The MVT rate is then determined by making weight measurements of moisture loss from the test media over a set time period, or measurement of the time of transfer of a known volume of liquid.

One issue with the above technique, however, is that the MVT rate measured using this system is proportional to the amount of moisture in the test media. For example, the MVT rate will be higher at the beginning of the test when the most moisture is present and lower as the test media dries out, and would go to zero if the test media is allowed to completely dry out. During this batch drying process, the moistened test media is exposed to an operating LAL mattress or other support system into which the moisture evaporates. This type of test takes place under dynamic or non steady-state conditions: the test media is charged with the moisture, which remains in the support system until dry. The weight of the test media is then measured as a function of time at the end of the drying process.

SUMMARY

Exemplary embodiments of the present disclosure are directed to apparatus, systems, and methods to measure a moisture vapor transfer rate of a test media and support system. Exemplary embodiments measure a parameter (for example, electrical conductivity) that is related to the amount of fluid in the test media. The parameter measurement can be compared to a parameter set point, and the amount of fluid in the test media adjusted so that the parameter measurement is brought closer to the set point (and the amount of fluid in the test media is maintained at a steady-state level). In certain exemplary embodiments, fluid is pumped or gravity-fed from a reservoir to the test media, and the flow rate is adjusted so that the parameter measurement is maintained at a steady-state value. In exemplary embodiments, the flow rate can be adjusted so that it is generally equivalent to the rate at which moisture vapor is transferred from the test media to the support system and surrounding environment.

Exemplary embodiments comprise a system having: a test media; a reservoir containing a fluid; a conduit between the reservoir and the test media, wherein the conduit is configured to supply the fluid from the reservoir to the test media; a sensor configured to measure a parameter and obtain a parameter measurement, wherein the parameter is related to an amount of the fluid in the test media; and a comparator configured to compare the parameter measurement to a parameter set point. Exemplary embodiments may also include a pump in fluid communication with the reservoir and the conduit, wherein the pump is configured to pump the fluid from the reservoir to the test media at an adjustable flow rate. Exemplary embodiments may also include a driver for the pump, wherein the driver is operable to adjust the flow rate. In exemplary embodiments, the amount of fluid in the test media can be changed so that the parameter measurement is brought closer in value to the parameter set point.

Exemplary embodiments may include a control valve in fluid communication with the conduit, wherein the control valve is configured to control a flow rate of the fluid from the reservoir to the test media, and the amount of fluid in the test media is changed so that the parameter measurement is brought closer in value to a parameter set point.

In exemplary embodiments, the parameter is electrical conductivity and the sensor is an ohm meter. The fluid may comprise an electrolyte in exemplary embodiments. Exemplary embodiments may include a support surface configured to support the test media and to transfer the fluid from the test media to the support surface.

Exemplary embodiments may also include a test media comprising a quantity of a fluid; a support system configured to support the test media and configured to transfer the fluid from the test media to the support system; a fluid addition system comprising a control system and a supply of the fluid; and a sensor configured to measure a parameter of the test media. In certain exemplary embodiments, the support system is a low air loss mattress. In exemplary embodiments, the parameter is related to the quantity of the fluid and the fluid addition system is configured to add the fluid from the supply to the test media at a fluid addition rate. In exemplary embodiments, the control system can be configured to control the fluid addition rate so that the parameter is maintained at a steady-state value. Certain exemplary embodiments include an air mover configured to provide a flow of air proximal to the support system. Exemplary embodiments may also include a sensor comparator configured to compare a measured value of the parameter to a desired value of the parameter.

Exemplary embodiments may also comprise a mass on the test media, wherein the mass is configured to simulate a patient load and a thermal heat supply configured to heat the fluid added from the supply to the test media. Exemplary embodiments may also comprise a reservoir containing the fluid and a pump configured to pump the fluid from the reservoir to the test media. In exemplary embodiments, the fluid addition rate can be altered by changing an operating parameter of the pump. Exemplary embodiments may also comprise a control valve and the fluid addition rate can be altered by opening or closing the control valve. In exemplary embodiments, the fluid addition system may comprise a reservoir configured to feed the fluid to the test media via gravity feed.

Exemplary embodiments may also comprise a method of measuring a moisture vapor transfer rate, the method comprising: providing a test media comprising a quantity of moisture; transferring moisture from the test media at a moisture transfer rate; measuring a parameter with a sensor to obtain a parameter measurement, wherein the parameter is related to the quantity of moisture comprised by the test media; adding a fluid to the test media at a flow rate; and controlling the flow rate so that the flow rate is generally equivalent to the moisture transfer rate.

Exemplary embodiments may also include providing an air mover and operating the air mover to provide an air flow proximal to the test media. Exemplary embodiments may also include supporting the test media with a support system and transferring the moisture from the test media to the support system. Exemplary embodiments may include comparing the parameter measurement to a parameter set point and controlling the flow rate so that the parameter measurement is adjusted to be closer in value to the parameter set point. In certain exemplary embodiments, the parameter is electrical conductivity and the sensor is an electrical conductivity meter.

BRIEF DESCRIPTION OF THE FIGURES

While exemplary embodiments of the present invention have been shown and described in detail below, it will be clear to the person skilled in the art that changes and modifications may be made without departing from the scope of the invention. As such, that which is set forth in the following description and accompanying figures is offered by way of illustration only and not as a limitation. The actual scope of the invention is intended to be defined by the following claims, along with the full range of equivalents to which such claims are entitled.

In addition, one of ordinary skill in the art will appreciate upon reading and understanding this disclosure that other variations for the invention described herein can be included within the scope of the present invention. For example, exemplary embodiments are disclosed with a fluid addition system comprising a pump and control valve. In other exemplary embodiments, the fluid addition system may comprise a reservoir and control valve configured to provide gravity-fed flow of fluid to the test media without the use of a pump. Still other exemplary embodiments may comprise a variable speed pump and no control valve. In addition, exemplary embodiments disclose a test media that is separate from the support system. Other exemplary embodiments may include a portion of the support system as the test media so that the test media is integral with the support system.

In the following Detailed Description of Disclosed Embodiments, various features are grouped together in several embodiments for the purpose of streamlining the disclosure. This method of disclosure is not to be interpreted as reflecting an intention that exemplary embodiments of the invention require more features than are expressly recited in each claim. Rather, as the following claims reflect, inventive subject matter lies in less than all features of a single disclosed embodiment. Thus, the following claims are hereby incorporated into the Detailed Description of Disclosed Embodiments, with each claim standing on its own as a separate embodiment.

The following Figures are referenced herein. The Figures illustrating the test systems of the present embodiments are not to scale.

Figure 1:
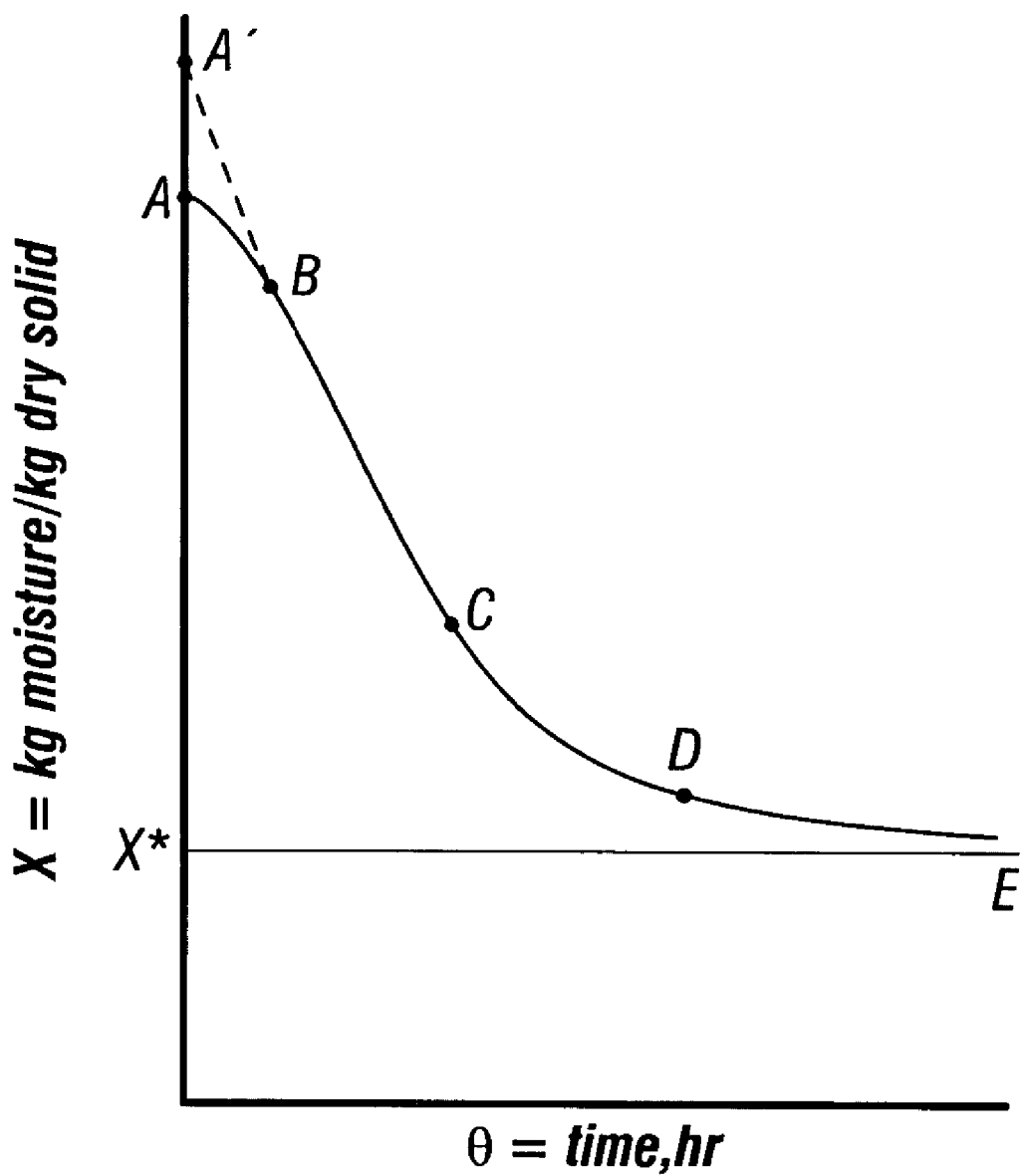

FIG. 1 provides a curve of moisture content as a function of time.

Figure 2:
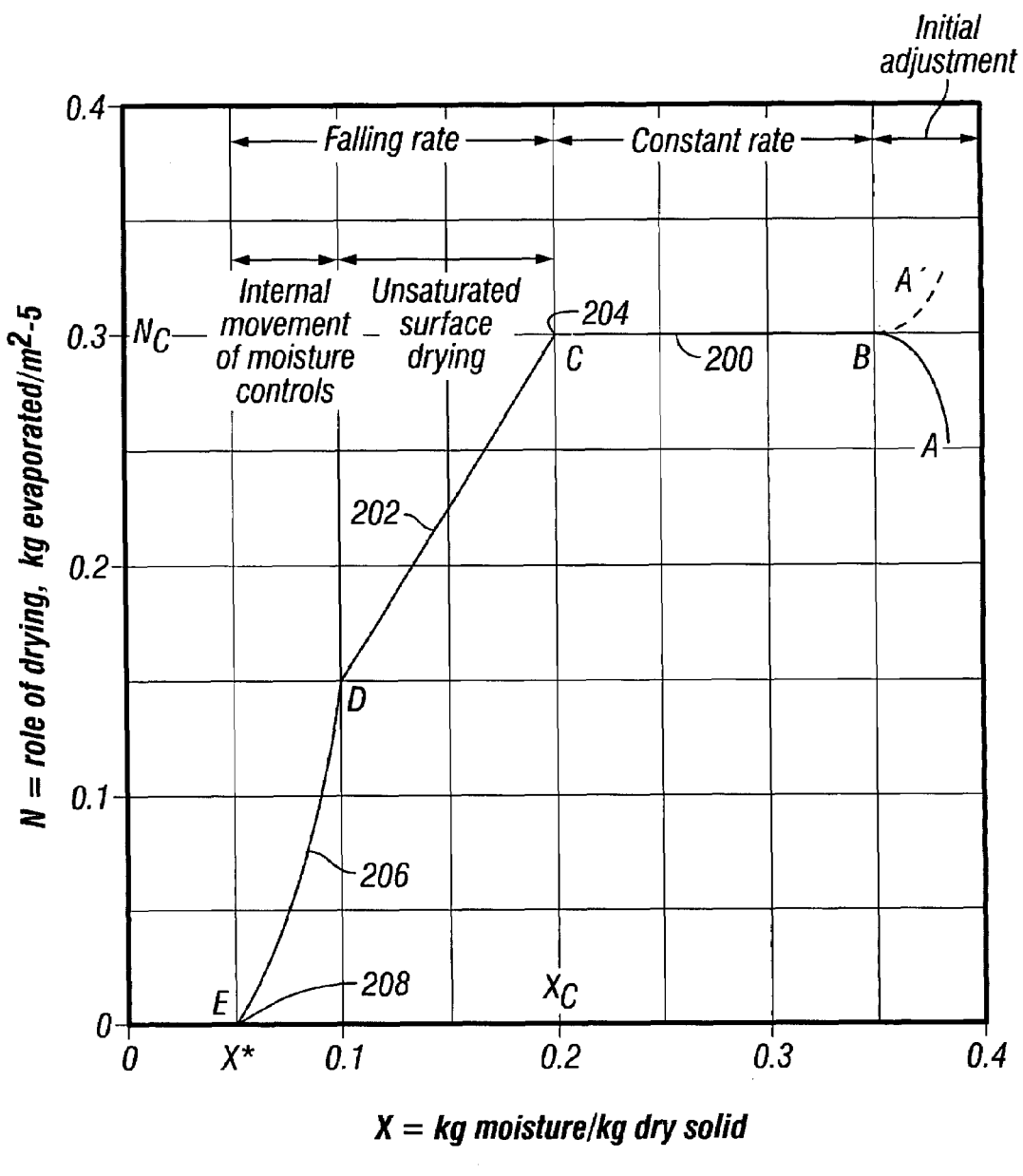

FIG. 2 provides a curve of a rate of drying (mass per area per time) as a function of moisture content.

Figure 3:
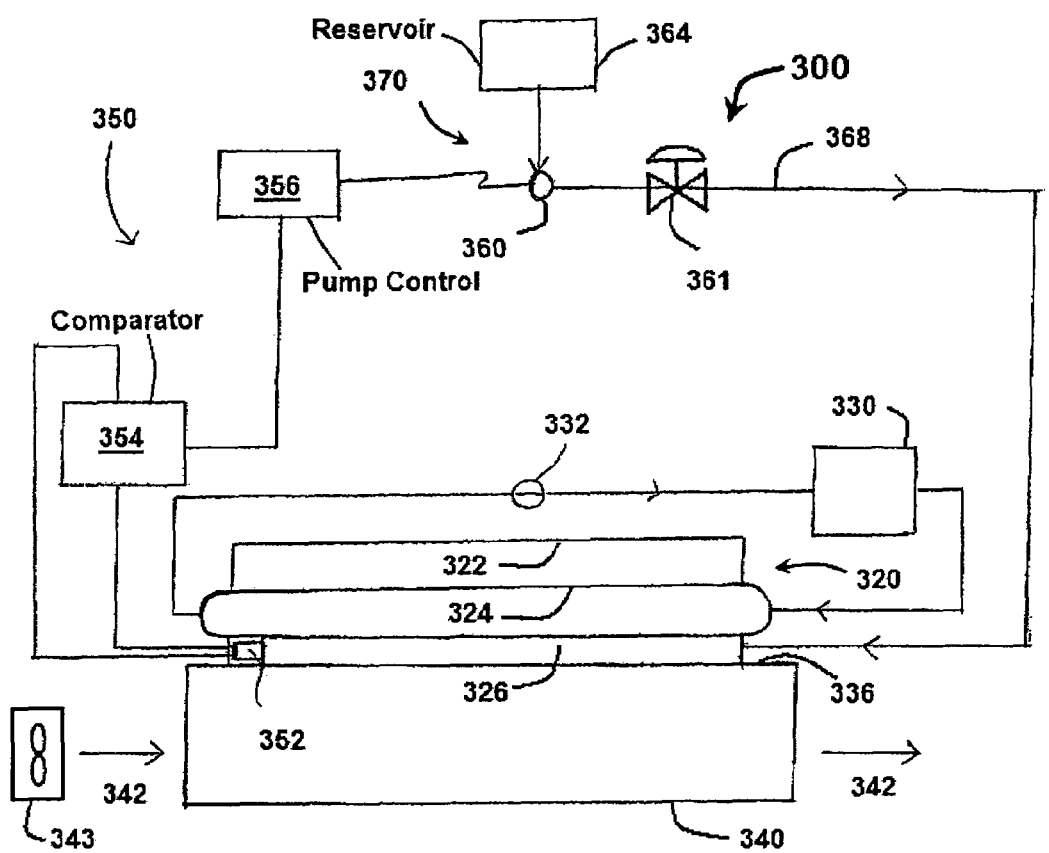

FIG. 3 provides an illustration of one exemplary embodiment of a test system according to the present disclosure.

Figure 4A:
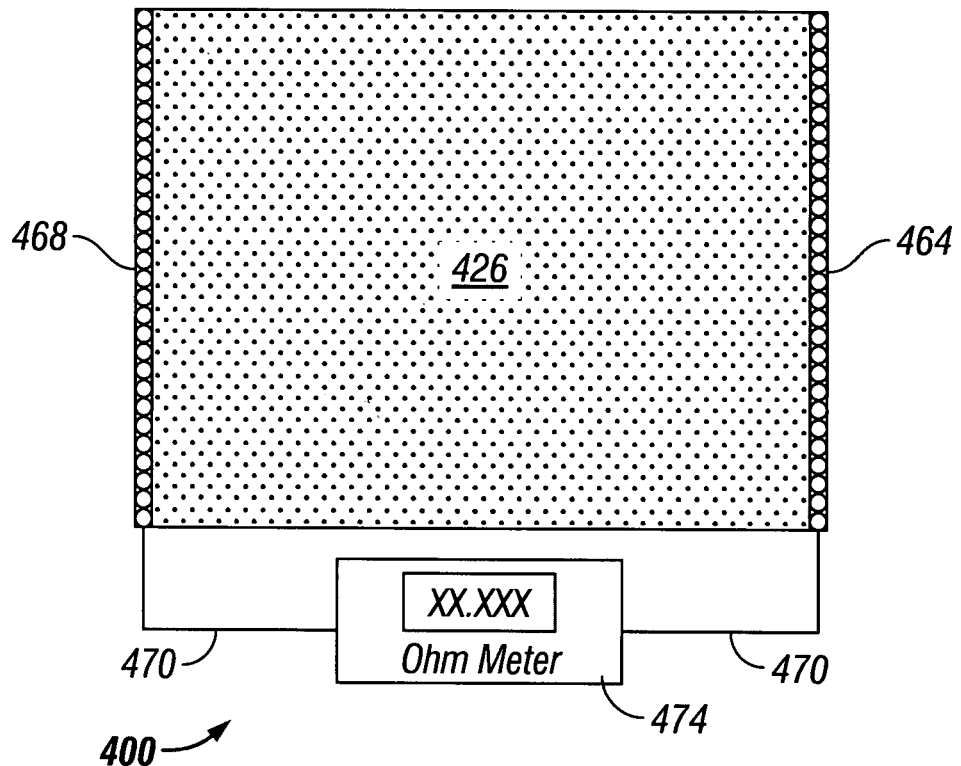

FIG. 4A provides an illustration of a top view of one exemplary embodiment of a test system according to the present disclosure.

Figure 4B:
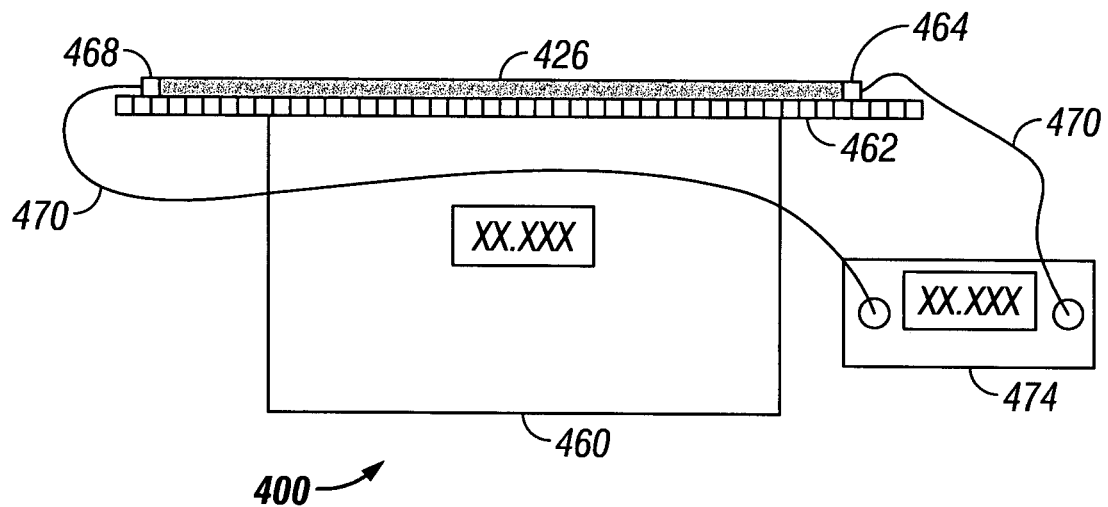

FIG. 4B provides an illustration of a side view of one exemplary embodiment of a test system according to the present disclosure.

FIG. 5 provides test results from the exemplary embodiment of the test system of FIGS. 4A and 4B.

Figure 6:
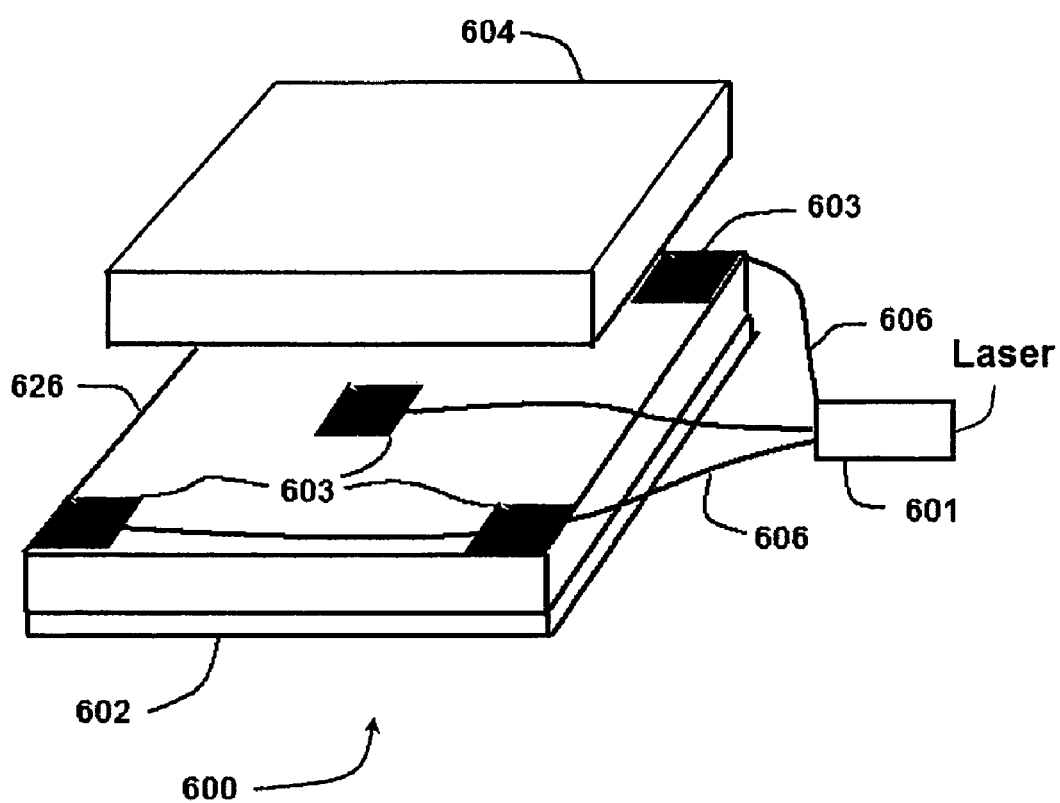

FIG. 6 provides an illustration of one exemplary embodiment of a test system according to the present disclosure.

Figure 7:
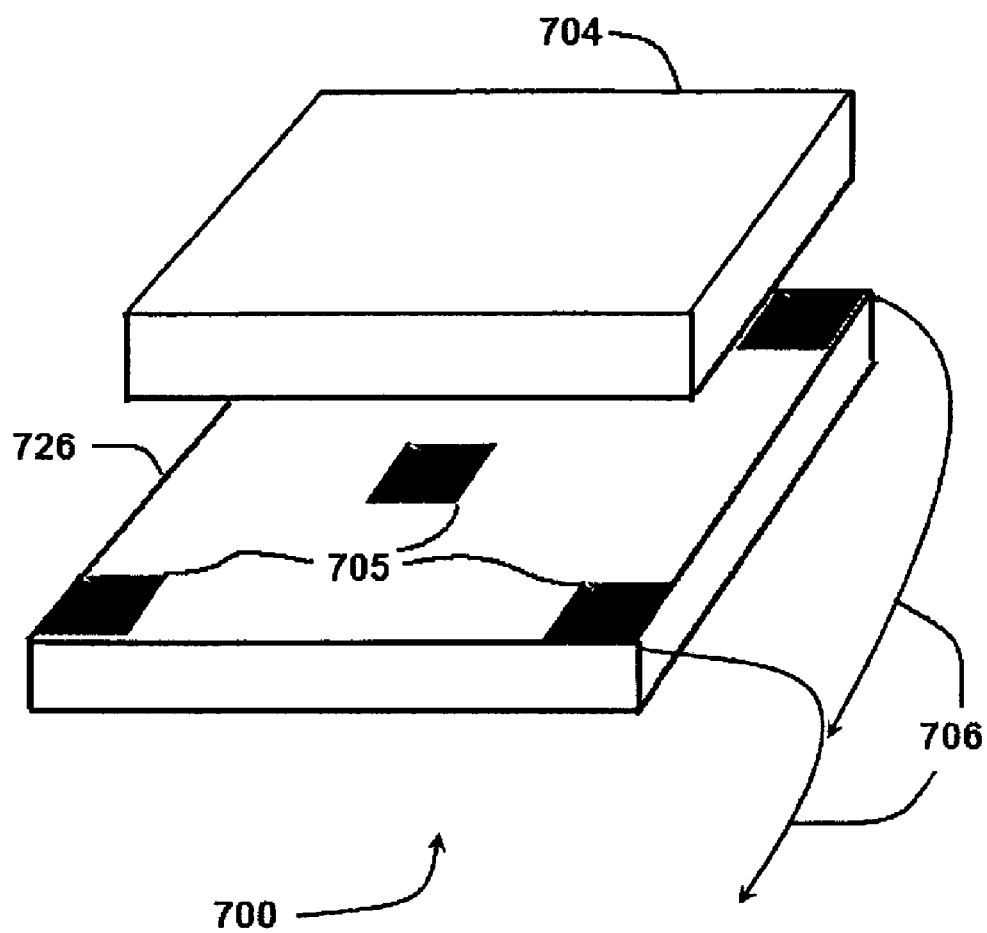

FIG. 7 provides an illustration of one exemplary embodiment of a test system according to the present disclosure.

Figure 8:
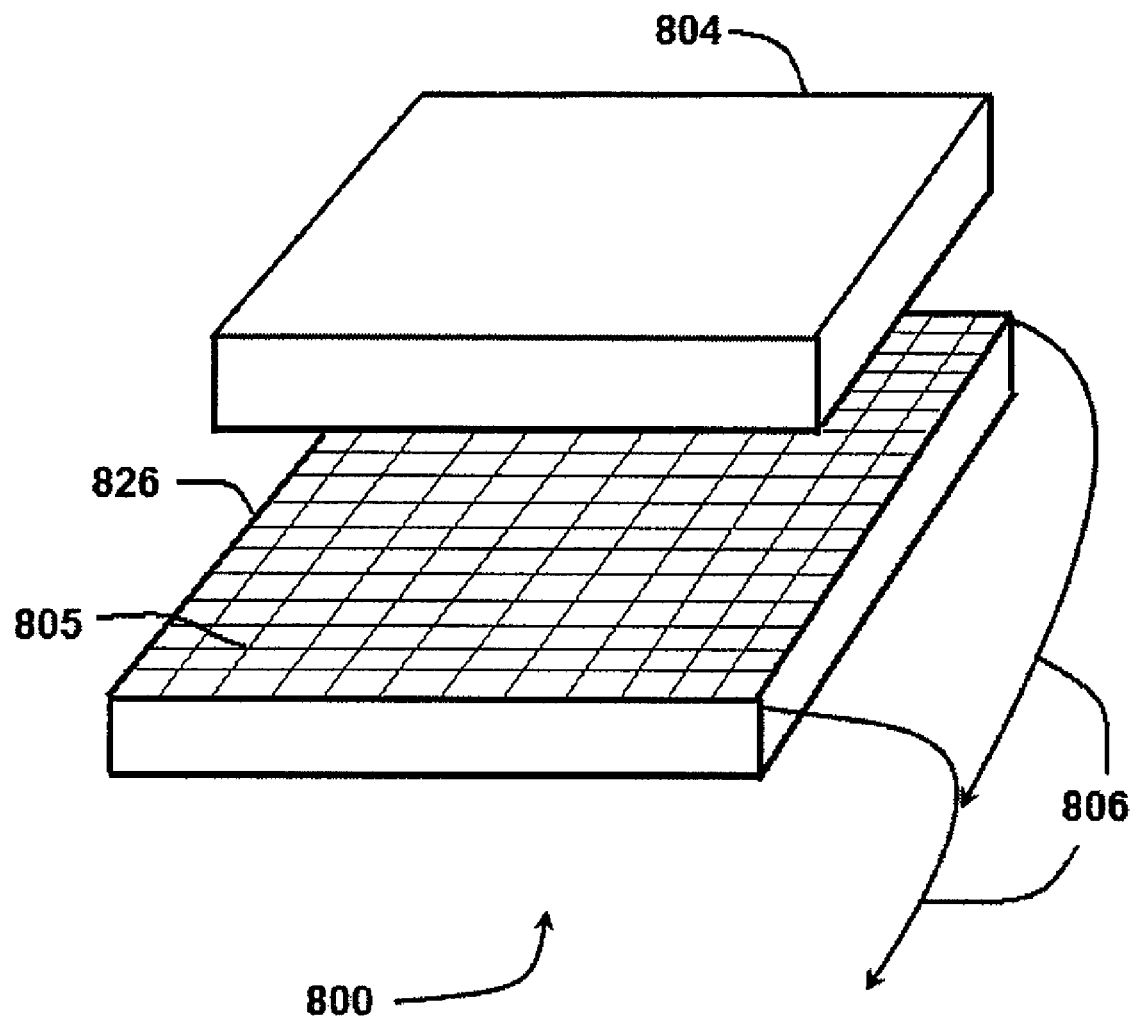

FIG. 8 provides an illustration of one exemplary embodiment of a test system according to the present disclosure.

Figure 9:
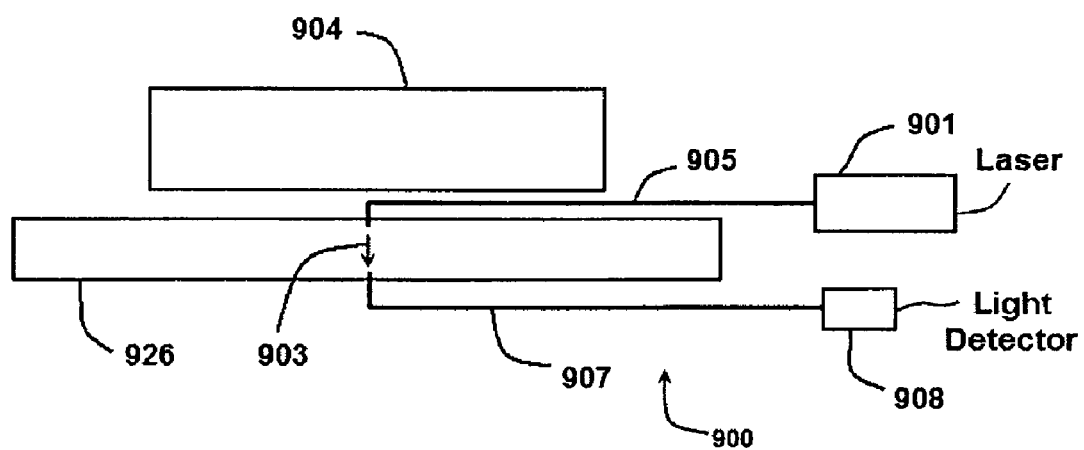

FIG. 9 provides an illustration of one exemplary embodiment of a test system according to the present disclosure.

DETAILED DESCRIPTION

Data obtained from a moisture vapor transfer test utilizing conventional methods and systems can yield a curve of moisture content as a function of time similar to that shown in FIG. 1. The data can then be converted into rates (or fluxes) of drying, expressed as the MVT rate (mass/(area)(time)), and plotted against moisture content, as illustrated in FIG. 2. This can be done by measuring the slopes of tangents drawn to the curve of FIG. 1 or by determining small changes in moisture content for corresponding small changes in time and calculating the rate.

There are two major parts of the rate curve of FIG. 2. First, there is an interval of a constant rate 200 and one of a falling rate 202. For the constant rate 200, the surface of the test media is exposed to relatively dry air, where there is a balance of the heat requirements for evaporation and the rate at which heat reaches the surface. Evaporation takes place from the surface of the test media. When the average moisture content of the test media has reached a value shown at 204 (Xc), the critical moisture content, the surface film of moisture on the test media has been so reduced by evaporation that further drying causes dry regions to form on the surface of the test media. These regions occupy increasingly larger proportions of the exposed test media as drying proceeds. Since, however, the MVT rate is computed with the constant gross surface of the test media, the value of the MVT rate falls even though the rate per unit of wet test media remains constant. A period of unsaturated surface evaporation from the test media results. This gives rise to falling rate interval 206, an interval of unsaturated surface drying. At 208, the moisture content of the test media has fallen to the equilibrium value for the prevailing air humidity, and drying stops.

This type of testing condition and process (e.g., in the falling rate region of FIG. 2), however, does not accurately simulate the actual conditions of a patient using a LAL mattress or other support system. In contrast, a patient on a support system typically perspires constantly. In addition, a patient typically perspires at an approximately constant rate. In other words, the patient's perspiration rate will not be reduced significantly over time as illustrated in FIG. 2, which documents conventional batch testing techniques for measuring the MVT rate.

In one exemplary embodiment of the present disclosure, the test media and test system allow for the replication and measurement of the MVT rate of a support system on which a perspiring human body resides. The batch process described above, however, only produces an average value that is skewed by choices of the initial amount of media moisture and the time frame for the test. As a result, measuring MVT rate in such a batch process provides inconsistencies in MVT rate measurements. Further, effects from other contributing variables, such as atmospheric pressure, relative humidity of the surrounding air, and temperature of surrounding air, are difficult to correlate.

Exemplary embodiments of the present disclosure provide a system and method that allow for the measurement of MVT rates in support systems and evaluation of external variables that effect MVT rate such as atmospheric pressure, relative humidity of the surrounding air, and temperature of surrounding air and fluid temperature. Exemplary embodiments of the present disclosure provide for a continuous process that allows for correlations of variables such as air flow, in addition to improved accuracies of MVT measurements. Exemplary embodiments of the present disclosure also allow for conditions that more closely resemble the actual conditions of a patient using an LAL mattress or other support system. To this end, exemplary embodiments allow for test media to be similarly supported in relation to the support system as it provides for a steady state MVT rate from the test media to the support system. In addition, exemplary embodiments of the present disclosure provide for continuous, reproducible, mechanistic, and controlled test methodology to evaluate and compare the moisture transport properties of a variety of support systems and/or the individual components of a LAL system (e.g., the coverlet, and/or mattress materials).

Exemplary embodiments of the present disclosure allow for a more realistic model by providing for a steady-state concentration of the moisture content (e.g., concentration) of the test media based on the metrics measured that are related to the amount of moisture in the test media. This steady-state operation provides that moisture concentrations at positions in the test media remain essentially constant with the passage of time. This steady-state operation is also less dependent of the characteristics and conditions of the support system and the environment in which it is tested and/or operated.

In exemplary embodiments, physical, optical and/or electrical parameters (metrics) that are related to or affected by the amount of moisture in the test media are quantitatively measured continuously (or periodically) during the analysis of the support system. In addition, moisture measurements are quantitatively measured continuously (or periodically) to provide values of the MVT rate across the test media and into the support system. The measurement of one or more of these parameters of the test media can then be used in a control loop system to maintain the amount of moisture in the test media at a steady state. In other words, the measurement of the parameter can be used to cause test fluid to be added to the test media so as to maintain equilibrium at a chosen point of moisture content. This in turn allows the test system, as discussed herein, to maintain a continuous steady MVT rate (e.g., the MVT rate is at steady state). This can be accomplished independent of the type of support system being evaluated.

In certain exemplary embodiments, measured parameters can include: electrical measurements such as conductance, resistance and/or capacitance; physical measurements such as Young's modulus and/or compression; and optical measurements such as refraction, IR scattering and pulsed photothermal radiometry. In other exemplary embodiments, other physical measurements are also possible, including measuring the weight of the test media. In exemplary embodiments, the measured parameter from the test media is related to, and varies in proportion to, the moisture content of the test media. As such, the measured parameter is also related to the MVT rate from the test media during a continuous moisture measurement test setting.

Using this correlation, the control loop system can then be used to add test fluid to the test media in a measured fashion (e.g., on a continuous or regular periodic and measurable basis) based on a predetermined set point of a desired moisture content level of the test media. In one exemplary embodiment, this predetermined set point can be selected to best replicate a human model. In one exemplary embodiment, the set point is based on setting a predetermined value for the MVT rate for the test media. The predetermined value of the MVT rate can be selected based on desired model criteria for testing the LAL mattress or other support system. Using established correlations, a predetermined value for the measured parameter that corresponds to the predetermined value of the MVT could then be used as the predetermined set point for the control loop system.

Moisture content of the test media can be continuously monitored in the control loop system by measuring one or more of the parameters as discussed herein. During operation of exemplary embodiments of the system, moisture is removed from the test media via vapor permeable characteristics of the support system such as a LAL mattress system and air flow through or proximal to the system. As the parameter measurements from the control loop system deviate from the set point (i.e., as the test media used with the LAL mattress system begins to dry during testing), the control loop system can then cause test fluid to be supplied to the test media. For example, processing circuits can receive a signal from a sensor that measures a parameter related to the moisture content of the test media. A fluid addition system can operate a pump or control valve in a manner to maintain a constant amount of the test fluid in the test media. In one exemplary embodiment, this can be done in a continuous (or regularly periodic) and measurable manner. In addition, process control techniques (e.g., proportional control, integral control, differential control and/or combinations thereof can be used to control the delivery of the test fluid to the test media. Once the system has stabilized, the fluid flow rate from the pump or control valve is generally established as the MVT rate for the LAL mattress system. This allows for a steady rate of moisture transport to be set and then maintained by the system. This approach is reproducible and provides a standardized method of handling the patient simulation.

As discussed herein, exemplary embodiments of the present disclosure can be applicable to different LAL mattress systems. In addition, exemplary embodiments of the present disclosure are also applicable with other mattress systems, including high-air-loss mattress systems, no-air-loss systems and/or other types of therapeutic support surfaces.

Exemplary embodiments of the present disclosure provide systems to evaluate and establish an MVT rate for a test media subjected to specific environmental conditions. The exemplary embodiment shown in FIG. 3 includes a measurement system 300 comprising a control system 350 and a fluid addition system 370. The exemplary embodiment shown also comprises a simulation system 320, which comprises a patient load simulator or mass 322 and a thermal heat supply 324. Other exemplary embodiments, however, may not comprise a simulation system, or may comprise a simulation system with different or fewer components. In this exemplary embodiment, a wetted test media 326 (which may be used to simulate human perspiration) is placed under simulation system 320 to simulate patient weight load and body temperature in a reproducible manner. Simulation system 320 can be used to mimic an average-sized torso having a regulated temperature and weight to provide proper mattress loading at the LAL mattress system-patient interface.

In one embodiment, mass 322 provides a weight of a suitable size to mimic that of a patient. The amount of weight provided by mass 322 can be adjustable. For example, mass 322 can be a fluid tight container (e.g., a bladder) from which a fluid, such as water, can be added or removed depending on the desired weight to be used in the testing. Alternatively, mass 322 could be disk shaped weights of known mass.

Thermal heat supply 324 is configured to provide enough thermal energy to simulation system 320 to allow it to operate at approximately normal human body temperature. Normal human body temperature is typically in the range of approximately 97 to 100 degrees Fahrenheit (36.1 to 37.8 degrees Celsius). In one exemplary embodiment, thermal heat supply 324 can include a fluid filled thermal blanket through which temperature controlled fluid is pumped. A heat source 330, such as a water bath and/or heating element, can be used to maintain the fluid temperature at the predetermined set point. The fluid can be pumped through thermal heat supply 324 through the use of a pump 332, such as a peristaltic, or rotary, fluid pump. Other pump mechanisms are also possible.

In exemplary embodiments, thermal heat supply 324 can be, or further include, an electrically resistive heating element, such as ceramic fiber heating mantles and/or heating tapes (not shown). In certain exemplary embodiments, a heat controller having a proportional-voltage control and thermocouple(s) can be used to maintain the desired temperature of the thermal heat supply.

In exemplary embodiments, test media 326 can include a porous and/or semi-porous material from which moisture can evaporate or transfer to the surrounding environment or support system. Test media 326 can be made of a flexible material, such as a woven, non-woven, felted, piled, and/or knit material, or a stiff or semi-stiff material. Examples of flexible materials include, but are not limited to, chamois (e.g., leather, natural fiber, and/or synthetic) and fabrics (natural fiber (e.g., cotton) and/or synthetic (e.g., rayon)). Examples of stiff and/or semi-stiff materials include, but are not limited to, rigid polymer sheets having a defined porosity, and/or a ceramic having a defined porosity. Regardless of the material selected, test media 326 may have a porosity that allows for a sufficient volume of the test fluid to be adsorbed into the media 326 to allow for testing of the support systems as discussed herein.

In the various exemplary embodiments, the test fluid can be a fluid capable of evaporation at temperatures and humidity levels typically found and/or encountered in hospital settings (i.e., settings where LAL mattress systems or other support systems are used). In addition, the test fluid can also include an electrolyte with one or more elements such as chlorine, bromine, and/or salts producing ion at concentrations sufficient to allow for measurement of electrical conduction through the test fluid. Examples of such test fluids include tap water (i.e., non-sterile water having the prevailing salts and minerals). Alternatively, the test fluid can be a saline solution such as sterile water with 0.9% w/v of NaCl, a dilute acetic acid solution (e.g., 1% v/v), or a Ringer's Saline. Other water based solutions having one or more types of salts are also possible. In exemplary embodiments, the conductive element in the fluid evaporates as the fluid evaporates. In certain exemplary embodiments, test media 326 may be initially wetted with a fluid that is identical to the fluid contained in the fluid addition system 370, while in other exemplary embodiments test media 326 may be initially wetted with a fluid that is different than the fluid contained in fluid addition system 370.

The test fluid can be used to wet test media 326, which can then be used to simulate perspiration from a patient's skin. In one embodiment, test media 326 is first weighed dry. Test media 326 can then be soaked (e.g., wetted) with the test fluid to at or below saturation (i.e., fluid does not drip from the test media). Test media 326 with test fluid can then be weighed to determine the weight of test fluid in test media 326.

Test media 326 can then be placed on a support surface 336 of a support system 340. In one exemplary embodiment, support system 340 is a LAL system and support surface 336 comprises a fabric cover formed from a Goretex™ fabric with the air cells of the LAL system adjacent the fabric cover. In the exemplary embodiment disclosed in FIG. 3, an air mover 343 provides air flow 342 proximal to support system 340.

Thermal heat supply 324 and patient load simulator 322 can then be placed over the test media 326, as illustrated in the exemplary embodiment shown in FIG. 3. As will be appreciated, the exact form of the simulation system 320 can be modified and/or changed to use different and/or additional components. Examples of such additional components include, but are not limited to use of one or more thermocouple sensors (not shown) connected to a readout device to monitor the uniformity of temperature regulation over the test media. In addition, a sensor (not shown) can be used to record ambient room temperature. As such, modifications and/or additions to the basic testing systems are well within the ability of one skill in the art.

As discussed herein, particular physical parameters are related to the amount of the test fluid in the test media 326. If the amount of moisture in test media 326 changes over a known period of time, an MVT rate can be established in the typical batch process previously described. However, if moisture is added to test media 326 at a known rate but the overall moisture content does not change (due to transfer of fluid from the test media to the surrounding environment, including support system 340), an MVT rate can also be established.

As illustrated, the exemplary embodiment of FIG. 3 also provides control system 350 that can be used to add fluid to test media 326 at a known rate and to maintain the moisture content of test media 326 at a specific amount. In exemplary embodiments, control system 350 includes a sensor comparator 354 that senses and/or receives signals from a sensor 352 that may be located in, on and/or adjacent test media 326. As discussed more fully below, sensor 352 can be used to measure a parameter of test media 326 that is related to the moisture content contained in test media 326. One example of such a parameter is the electrical conductivity of test media 326; other exemplary embodiments may measure different parameters.

Sensor comparator 354 can operate to compare the signals received from sensor 352 to a set point for the given physical parameter that corresponds to the specific quantity of moisture or fluid desired in test media 326. In one embodiment, this can be accomplished with a computer having a processor and circuitry that controls input and output signals.

In the exemplary embodiment shown in FIG. 3, a reservoir 364 supplies the test fluid to a pump 360. In exemplary embodiments, sensor comparator 354 can be operatively coupled to a pump control 356 that can control the flow rate of a pump 360. In certain exemplary embodiments, pump 360 can be a peristaltic or other type of pump that creates flow in a "pulsed" manner. Pump control 356 may control the flow rate by varying an operating parameter such as the length of the flow pulses or the time in between the pulses. In certain exemplary embodiments, pump control 356 may vary the operating speed of pump 360 and/or adjust a control valve 361 to control the amount of fluid provided to test media 326. The operating speed of pump 360 may be varied by adjusting the speed of an electric motor (not shown) or other pump driver. Sensor comparator 354 can also execute the process control techniques as discussed herein.

As discussed, the sensor comparator 354 can operate to compare the signals received from the test media 326 to the set point for the given physical parameter that corresponds to desired quantity of fluid in test media 326. Sensor comparator 354 can then cause pump 360 to provide the test fluid to test media 326 through a conduit or supply line 368. In one embodiment, the test fluid can be diffused through test media 326 using two or more outlets from the supply line 368.

When system 300 is operating under steady-state conditions, fluid will be transferred from test media 326 to the surrounding environment (including support system 340) at the generally the same rate that fluid is being added to test media 326 from reservoir 364. The flow rate of fluid from reservoir 364 to test media 326 can therefore be used to establish the MVT rate for support system 340 for the given operating conditions. The fluid flow rate can be determined by any number of methods known to those skilled in the art. For example, a flow meter may be used to directly measure the flow rate, or the fluid level or mass in reservoir 364 can be tracked over time to establish the fluid flow rate.

Other exemplary embodiments may comprise other methods and apparatus for determining the fluid flow rate. In one exemplary embodiment, sensor comparator 354 can operate to cause pump 360 to be stepped to maintain a relatively constant or steady-state value of the received signal from sensor 352. Each step of the pump 360 can be correlated to a known amount of the test fluid that is added to the test media. Sensor comparator 354 can determine the unit weight per time interval for the area of the test media, which can be used to establish the MVT rate for a steady state condition.

In exemplary embodiments, typical physical parameters that can be sensed by sensor 352 include, but are not limited to: electrical measurements such as capacitance, resistance and/or conductivity (conductance); physical parameters such as Young's modulus and/or compression; optical measurements such as refraction, IR scattering and pulsed photothermal radiometry. In certain exemplary embodiments, other physical measurements are also possible, including measuring weight of the test fluid in the test media.

In one exemplary embodiment, compression of the test media allows for physical property changes in the test media to be measured as the amount of the test fluid in the test media changes under the compression. In another exemplary embodiment, light transmittance can be used as the measured parameter. Light transmittance is the fraction of incident light at a specified wavelength that can pass through a sample, such as the test media. Light transmittance can be quantified by T=I/Io, where Io is the intensity of the incident light and I is the intensity of the light that passes through the sample. Subsurface scattering occurs when light penetrates a material's surface and is reflected several times at irregular angles inside the material. The light is then emitted at a different angle than it would have been had it reflected directly off the surface.

An additional useful metric for correlating MVT rate is that of capacitance of the test media. Capacitance can exist between two conductors insulated from one another. The formula below defining capacitance is valid if it is understood that the conductors have equal but opposite charge Q, and the voltage V is the potential difference between the two conductors. Capacitance is the measure of electrical charge stored for a given electrical potential, and is defined as:

$$C=e(A/d)$$

where C is the capacitance, e is the permittivity of the material between the plates (i.e., the dielectric constant), A is the surface area of one of the plates, and d is the separation distance between the two plates. As the test fluid evaporates from the test media, the dielectric constant of the wetted test media changes proportionally to the amount of test fluid evaporating and thus the capacitance of the system decreases depending upon the amount of fluid lost.

As previously mentioned, electrical conductivity (or resistance) of a test media can be used as a parameter to determine the quantity of fluid in the test media. FIGS. 4A and 4B provide an illustration of a test system 400 used to determine the relationship of conductivity verses the quantity of fluid in a test media 426 over a time interval. FIG. 4A provides a top view, while FIG. 4B provides a side view of test system 400. As illustrated in FIG. 4B, an electronic scale 460 with a support surface 462 may be used to verify the results obtained with ohm meter 474. Other exemplary embodiments may not include an electronic scale to verify the results. In the exemplary embodiment shown, test media 426 includes a first and second electrical contact (e.g., braided copper wire) 464 and 468 coupled at or adjacent opposite sides, or edges, of the test media 426. Electrical leads 470 couple electrical contacts 464 and 468 to an ohm meter 474 that can be used to record the change in resistance across test media 426 as the amount of fluid in test media 426 changes. In the exemplary embodiment shown in FIGS. 4A and 4B, signals from the scale 460 can be used to record the changes in weight of the test media 426 as the amount of fluid changes.

In one exemplary experiment using the test system 400, test media 426 (in this experiment, a chamois) was saturated with a 3 g/L saline solution and rung out to leave 95 grams of saline solution and a resistance of 44 Ohms. Test media 426 was then allowed to dry over a period of three hours, and weight measurements of test media 426 were taken at fifteen minute time intervals. Test results indicate the conductivity of test media 426 changed as the amount of fluid in test media 426 changed. The relationship between the two variables allows for a correlation to be established between conductivity and fluid content in test media 426.

In an additional exemplary experiment, water having conductivity from chlorination was selected as the test fluid. Data from the experiment is provided in FIG. 5. The data demonstrates that as the amount of fluid in the test media decreased, the normalized conductivity measured across the test media also decreased. In addition, as the amount of fluid in the test media decreased, the resistance measured across test media increased.

Additional exemplary embodiments of test systems are shown in FIGS. 6-9.

FIG. 6 illustrates a method for implementing a compression test into a continuous MVT setting for LAL mattress evaluation. In this exemplary embodiment test system 600 allows the thickness of the test media to be measured continuously. Test system 600 comprises a laser 601, a mirror 602, and one or more photo detectors 603. In addition a mass 604 is placed on a test media 626. Light from laser 601 can be directed in between mass 604 and test media 626 using fiber optic cables 606. Laser 601 can then be pulsed through test media 626. After a light pulse from laser 601 passes through test media 626, it can be reflected by mirror 602 beneath the test media and back up to photo detector 603 connected to a computer running a program that would measure the distance the laser pulse passed. A number of different points (e.g., five different points in the exemplary embodiment shown) on test media 626 can be measured and then averaged to give an accurate picture of the compression of the entire test media 626. Similar to previously-described exemplary embodiments, the amount of fluid being added to test media 626 during testing can be controlled so that the thickness of test media 626 is maintained at a constant value. The flow rate of the fluid being added can then be used to establish the MVT rate of a support system used to support test media 626.

FIG. 7 illustrates an exemplary embodiment of a test system 700 that measures capacitance of a test media 726. The capacitance can then be used as a correlation to the amount of fluid in test media 726. In this exemplary embodiment, capacitive plates 705 are placed between test media 726 and mass 704. In the exemplary embodiment shown, capacitive plates 705 are connected to wire leads 706 that are attached to a NI Daq board and computer (not shown). In the exemplary embodiment shown, measurements can be collected from capacitive plates 705 and averaged to give an overall capacitance reading, which can be correlated to the amount of fluid in test media 726. In certain exemplary embodiments, it may be beneficial to place acrylic spray on capacitive plates 705 to allow charge to accumulate on the plates. Again, the MVT rate for a support system can be established by measuring the flow rate needed to maintain the capacitance at a steady-state value.

Another exemplary embodiment of a test system 800 for measuring capacitance is illustrated in FIG. 8. In this exemplary embodiment, a wire mesh 805 is placed in between test media 826 and mass 804 and is also placed in between test media 826 and a Goretex™ covering of a support system (not shown) beneath test media 826. It is believed that wire mesh 805, although flexible in structure, will be able to maintain a constant shape and distance with the changing of test media 826 due to the equally distributed load placed on top of it. In the exemplary embodiment shown, wire leads 806 can be connected to wire mesh 805 and to a NI Daq board and computer (not shown) for continuous data collection. In certain exemplary embodiments, LabVIEW™ or a similar program would then be used to collect the capacitance data. In certain exemplary embodiments, it may be beneficial to place acrylic spray on wire mesh 805 to allow charge to accumulate on it.

The exemplary embodiment of a test system 900 is shown in FIG. 9 comprises a test media 926 under a mass 904. This embodiment is similar to the exemplary embodiment shown in FIG. 6. For example a laser 901 transmits a light beam 903 through fiber optic cables 905 between mass 904 and test media 926. However, in FIG. 9, instead of being reflected from a mirror, light beam 903 is allowed to transmit through test media 926 and to a second fiber optic cable 907 to a light detector 908 (e.g., sensor) on the other side of test media 926.

The invention claimed is:

1. A system comprising:
   a test media;
   a reservoir containing a fluid;
   a conduit between the reservoir and the test media, wherein the conduit is configured to supply the fluid from the reservoir to the test media;
   a sensor configured to measure a parameter and obtain a first measurement of the parameter, wherein the parameter is related to an amount of the fluid in the test media; and
   a comparator configured to receive the first measurement of the parameter and compare the first measurement of the parameter to a set point of the parameter.

2. The system of claim 1, further comprising a support surface configured to support the test media.

3. The system of claim 1, further comprising:
   a pump in fluid communication with the reservoir and the conduit, wherein the pump is configured to pump the fluid from the reservoir to the test media at an adjustable flow rate.

4. The system of claim 3, further comprising:
   a driver for the pump, wherein the driver is operable to adjust the adjustable flow rate.

5. The system of claim 4, wherein the sensor is configured to obtain a second measurement of the parameter after the amount of fluid in the test media is changed, and wherein the second measurement of the parameter is closer in value to the set point of the parameter than is the first measurement of the parameter.

6. The system of claim 1, further comprising:
   a control valve in fluid communication with the conduit, wherein:
   the control valve is configured to control a flow rate of the fluid from the reservoir to the test media; and
   the sensor is configured to obtain a second measurement of the parameter after the amount of fluid in the test media is changed, and wherein the second measurement of the parameter is closer in value to the set point of the parameter than is the first measurement of the parameter.

7. The system of claim 1 wherein the parameter is electrical conductivity.

8. The system of claim 1 wherein the sensor is an ohm meter.

9. The system of claim 1 wherein the fluid comprises an electrolyte.

10. The system of claim 1, further comprising a mass on the test media, wherein the mass is configured to simulate a patient load.

11. The system of claim 1, further comprising a thermal heat supply configured to heat the fluid.

12. A system comprising:
   a test media comprising a quantity of a fluid;
   a support system configured to support the test media;
   a fluid addition system comprising a control system and a supply of the fluid; and
   a sensor configured to obtain a first measurement of a parameter of the test media, wherein:
   the parameter is related to the quantity of the fluid;
   the fluid addition system is configured to add the fluid from the supply to the test media at a fluid addition rate; and
   the control system is configured to control the fluid addition rate so that the parameter is maintained at a steady-state value.

13. The system of claim 12, further comprising an air mover configured to provide a flow of air proximal to the support system.

14. The system of claim 12, wherein the parameter is electrical conductivity.

15. The system of claim 12 wherein the sensor is an ohm meter.

16. The system of claim 12 wherein the control system comprises a sensor comparator configured to compare a measured value of the parameter to a desired value of the parameter.

17. The system of claim 12 wherein the support system is a low air loss mattress.

18. The system of claim 12, further comprising a mass on the test media, wherein the mass is configured to simulate a patient load.

19. The system of claim 12, further comprising a thermal heat supply configured to heat the fluid added from the supply to the test media.

20. The system of claim 12 wherein the fluid addition system further comprises:
   a reservoir containing the fluid; and
   a pump configured to pump the fluid from the reservoir to the test media.

21. The system of claim 20 wherein the fluid addition rate can be altered by changing an operating parameter of the pump.

22. The system of claim 12, wherein the control system comprises a control valve and the fluid addition rate can be altered by opening or closing the control valve.

23. The system of claim 12, wherein the fluid addition system further comprises a reservoir configured to feed the fluid to the test media via gravity feed.

24. A method of measuring a moisture vapor transfer rate, the method comprising:
   providing a test media comprising a quantity of moisture;
   transferring moisture from the test media at a moisture transfer rate;
   measuring a parameter with a sensor to obtain a parameter measurement, wherein the parameter is related to the quantity of moisture comprised by the test media;
   adding a fluid to the test media at a flow rate; and
   controlling the flow rate so that the flow rate is generally equivalent to the moisture transfer rate.

25. The method of claim 24, further comprising:
   providing an air mover; and
   operating the air mover to provide an air flow proximal to the test media.

26. The method of claim 24, further comprising:
   supporting the test media with a support system; and
   transferring the moisture from the test media to the support system.

27. The method of claim 24, further comprising:
   comparing the parameter measurement to a set point of the parameter;
   controlling the flow; and
   obtaining a second parameter measurement that is closer in value to the parameter set point than is the first parameter measurement.

28. The method of claim 24, wherein the parameter is electrical conductivity.

29. The method of claim 24, wherein the sensor is an electrical conductivity meter.

* * * * *